(12) United States Patent
Mankovich

(10) Patent No.: US 12,353,371 B2
(45) Date of Patent: Jul. 8, 2025

(54) ASSESSING QUALITY OF GENOMIC REGIONS STUDIED FOR INCLUSION IN STANDARDIZED CLINICAL FORMATS

(71) Applicant: KONINKLIJKE PHILIPS N.V., Eindhoven (NL)

(72) Inventor: Alexander Ryan Mankovich, Somerville, MA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

(21) Appl. No.: 18/073,863

(22) Filed: Dec. 2, 2022

(65) Prior Publication Data
US 2023/0177028 A1    Jun. 8, 2023

Related U.S. Application Data

(60) Provisional application No. 63/285,684, filed on Dec. 3, 2021.

(30) Foreign Application Priority Data

Dec. 27, 2021    (EP) .................................... 21217876

(51) Int. Cl.
| | | |
|---|---|---|
| *G06F 16/215* | (2019.01) | |
| *G06F 16/25* | (2019.01) | |
| *G16B 30/00* | (2019.01) | |
| *G16B 50/10* | (2019.01) | |

(52) U.S. Cl.
CPC .......... *G06F 16/215* (2019.01); *G06F 16/258* (2019.01); *G16B 30/00* (2019.02); *G16B 50/10* (2019.02)

(58) Field of Classification Search
CPC ..... G06F 16/215; G06F 16/258; G16B 30/00; G16B 50/10; G16B 20/20; G16B 50/00
See application file for complete search history.

(56) References Cited

U.S. PATENT DOCUMENTS

| | | | |
|---|---|---|---|
| 2013/0185096 A1* | 7/2013 | Giusti .................... | G06Q 10/10 705/3 |
| 2016/0026753 A1* | 1/2016 | Krishnaswami ....... | G16B 20/20 702/19 |
| 2017/0177804 A1* | 6/2017 | Lee ......................... | G16Z 99/00 |
| 2017/0286594 A1 | 10/2017 | Reid | |
| 2018/0285391 A1* | 10/2018 | Juneja ................. | G06F 16/2282 |
| 2019/0024161 A1 | 1/2019 | Lu | |

(Continued)

OTHER PUBLICATIONS https://genome.ucsc.edu/FAQ/FAQformat.html#format1, 2000.
(Continued)

*Primary Examiner* — Maher N Algibhah

(57) ABSTRACT

A method for assessing quality of genomic regions studied for inclusion in standardized clinical formats includes receiving data sets to be applied to a plurality of gene panels. The method also includes applying, by a processor executing instructions, standardized quality control metrics to the data sets to be applied to the plurality of gene panels; filtering, by the processor executing the instructions, each of the data sets to be applied to the plurality of gene panels to sets of variants and formatting the sets of variants in a clinical format, and outputting the sets of variants resulting from the filtering to a downstream application.

16 Claims, 5 Drawing Sheets

(56) References Cited

U.S. PATENT DOCUMENTS

| | | |
|---|---|---|
| 2019/0026433 A1 | 1/2019 | Lu |
| 2019/0127807 A1 | 5/2019 | Suzuki |
| 2020/0105365 A1 | 4/2020 | Glode |
| 2020/0258601 A1 | 8/2020 | Lau |
| 2021/0343372 A1 | 11/2021 | Tell |

OTHER PUBLICATIONS

Milius, Robert P. et al "Histoimmunogenetics Markup Language 1.0: Reporting next generation sequencing-based HLA and KIR genotyping", Human Immunology, vol. 76, pp. 963-974, 2015.

Muller, Heiko et al "VCF.Filter: interactive prioritization of disease-linked genetic variants from sequencing data", Nucleic Acids Research, vol. 45, 2017.

Yan, Melissa Y. et al "VariantQC: A Visual Quality Control Report for Variant Evaluation", Bioinformatics, vol. 35, No. 24, 2019, pp. 5370-5371.

\* cited by examiner

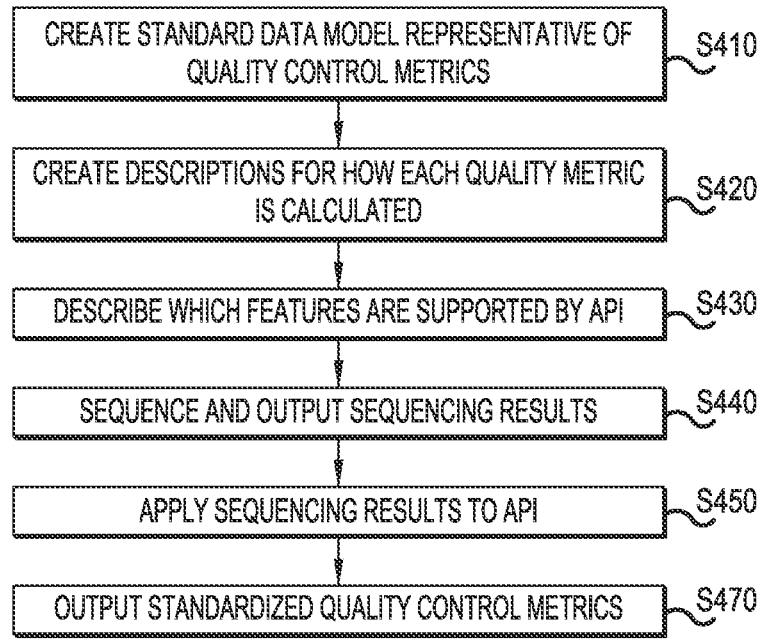
FIG.4A
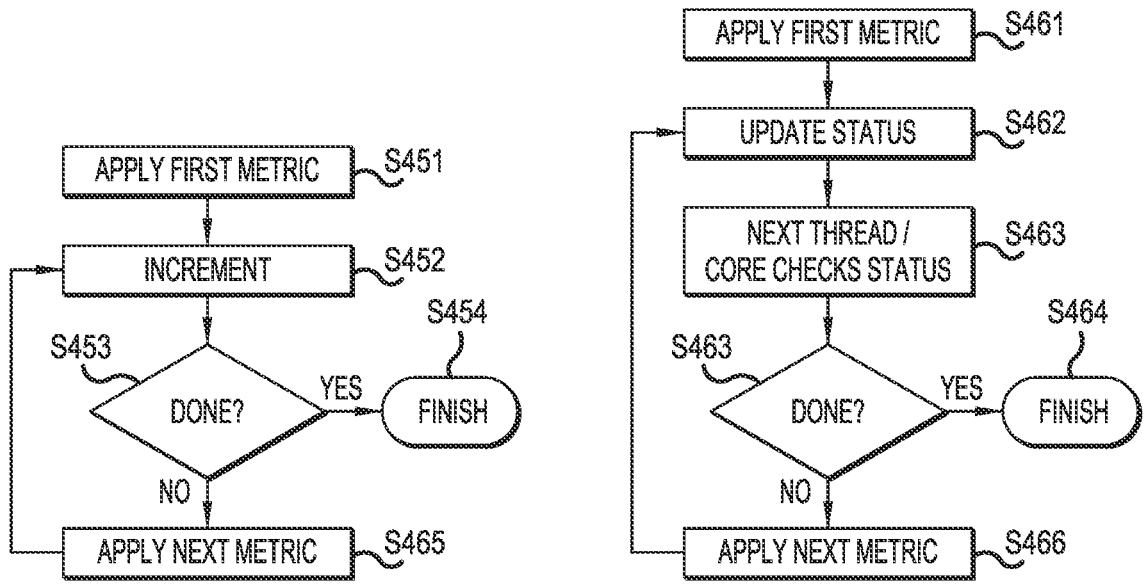
FIG.4B
FIG.4C

ASSESSING QUALITY OF GENOMIC REGIONS STUDIED FOR INCLUSION IN STANDARDIZED CLINICAL FORMATS

BACKGROUND OF THE INVENTION

A genome is the complete set of nucleotide sequences of an organism's DNA. Genes are sequences of nucleotides known as coding regions of a genome, whereas chromosomes contain many genes. The human genome contains about 3 billion base pairs of nucleotides that make up all of the chromosomes of an individual. The nucleotides are A (Adenine), T (Thymine), C (Cytosine) and G (Guanine). The base pairs are A and T, and C and G. The pairing serves as the underlying basis for how DNA molecules are copied when cells divide. The pairing also serves as the underlying basis for typical DNA analysis.

Gene panel analysis is a common bioinformatics analysis used to identify variations in genes. Variations in genes are sought since the variations may have clinical significance. A sequenced sample genome is inspected in specific ranges, and checked for deviations from the reference genome. One aspect of gene analysis is quality control: ensuring that the finding of the presence or absence of a nucleotide at a particular position is the correct finding. In the United States, all clinical laboratories must have a validated quality control process, though the process may vary from one institution to another.

Multiple different data formats are used in bioinformatic analyses, including .FASTQ, .BAM, .VCF and .BED. A gene panel is commonly represented in a .BED file as a set of genome ranges. In a .BED file, required fields include the chromosome, start position of each genome range and end position of each genome range. .FASTQ is a text-based format for storing a nucleotide sequence and corresponding quality control scores. .BAM is a compressed binary file used to represent aligned sequences up to 128 Mb. .VCF stands for variant call format and is a text-based format for storing gene sequence variations. .BED stands for browser extensible data and is a text-based format for storing genomic regions as coordinates and associated annotations. Data formats used in bioinformatic analyses are de facto standards for representation of genomic data and metadata for software used in many bioinformatics workflows. However, the usefulness of such data formats varies and is sometimes lacking. For example, the data formats are sometimes not convertible to appropriate representations as clinical records in the clinical realm. Formats such as .VCF and .BED are designed more for readability and complete representation than efficiency and extensibility.

Additionally, storage of the total contents of an underlying file in the clinical record is often unnecessary. In a typical clinical scenario, a .VCF file containing genetic variants is further filtered to a set of actionable variants or potentially actionable variants, and the findings are stored outside the VCF file in a clinical format which is optimized for clinical purposes. In clinical laboratories, genetic variants are only reportable if the genetic variants meet certain quality control standards.

The quality control requirements for bioinformatic data are often met by storing the data of genomic regions in a .BED file. The required quality control metadata corresponding to the informatic data is typically stored separately. However, there is no standardized mechanism for retrieving studied regions, resolving whether regions to be reported meet quality control metadata requirements, and providing only the filtered data to downstream applications.

SUMMARY OF THE INVENTION

The invention is defined by the claims. Dependent claims represent beneficial embodiments of the invention.

A method for assessing quality of genomic regions studied for inclusion in standardized clinical formats includes receiving data sets to be applied to a plurality of gene panels is disclosed. The method also includes applying, by a processor executing instructions, standardized quality control metrics to the data sets to be applied to the plurality of gene panels; filtering, by the processor executing the instructions, each of the data sets to be applied to the plurality of gene panels to sets of variants and formatting the sets of variants in a clinical format, and outputting the sets of variants resulting from the filtering to a downstream application.

According to an aspect of the present disclosure, a server for assessing quality of genomic regions studied for inclusion in standardized clinical formats includes a memory and a processor. The memory stores instructions and data sets to be applied to a plurality of gene panels. The processor processes the instructions and reads the data sets to be applied to the plurality of gene panels. When executed by the processor, the instructions cause the server to execute a process comprising receiving data sets to be applied to the plurality of gene panels, and storing the data sets to be applied to the plurality of gene panels in the memory; applying standardized quality control metrics to the data sets to be applied to the plurality of gene panels; filtering, by the processor executing the instructions, each of the data sets to be applied to the plurality of gene panels to sets of variants and formatting the sets of variants in a clinical format, and outputting the sets of variants resulting from the filtering to a downstream application.

According to an aspect of the present disclosure, a computer-readable medium that stores instructions for assessing quality of genomic regions studied for inclusion in standardized clinical formats is disclosed. Alternatively or additionally, a computer program product is performing the steps of the computer-readable medium. When executed by a processor, the instructions cause a computer to: receive data sets to be applied to the plurality of gene panels, and store the data sets to be applied to the plurality of gene panels in a memory; apply standardized quality control metrics to the data sets to be applied to the plurality of gene panels; filter each of the data sets to be applied to the plurality of gene panels to sets of variants and format the sets of variants in a clinical format, and output the sets of variants resulting from the filtering to a downstream application.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements. The following figures help in describing the invention:

FIG. 4A illustrates a method for assessing quality of genomic regions studied for inclusion in standardized clinical formats, in accordance with a representative embodiment.

FIG. 4B illustrates a processing method for assessing quality of genomic regions studied for inclusion in standardized clinical formats, in accordance with a representative embodiment.

FIG. 4C illustrates another processing method for assessing quality of genomic regions studied for inclusion in standardized clinical formats, in accordance with a representative embodiment.

DETAILED DESCRIPTION OF EMBODIMENTS

Figure 1A:
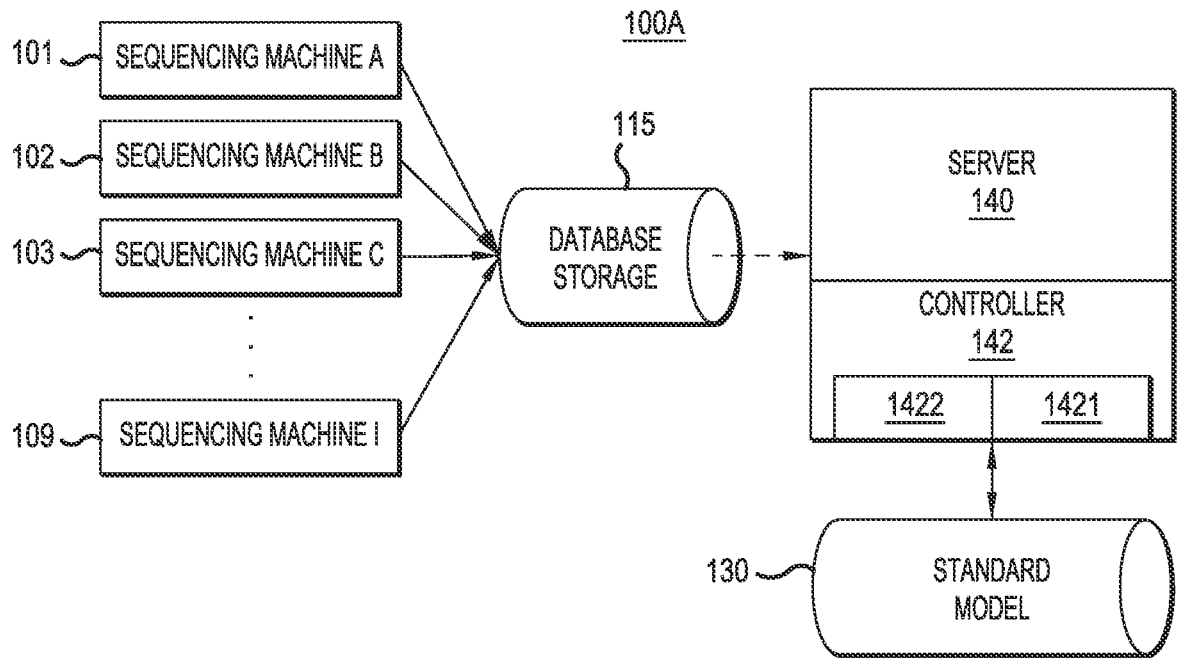
FIG. 1A illustrates a system for assessing quality of genomic regions studied for inclusion in standardized clinical formats, in accordance with a representative embodiment.

In one aspect of the present invention, a method for assessing quality of genomic regions studied for inclusion in standardized clinical formats is disclosed. The method comprises:
receiving data sets of/from a plurality of gene panels;
applying, by a processor executing instructions, standardized quality control metrics to the data sets of/from the plurality of gene panels;
filtering, by the processor executing the instructions, the data sets to sets of variants based on the standardized quality control metrics, and formatting the sets of variants in a clinical format, and
outputting the sets of variants resulting from the filtering to a downstream application.

In some embodiments, the filtering can be done on set of variants not meeting certain quality control criteria.

In some embodiments, the data sets are received, that are to be applied to the plurality of gene panels. It is to be understood, that "of/from" and "to be applied to" are synonyms within the context of the present application. Hence, when "to be applied to" is used, this can be interpreted as "of/from"

Further, there will be details explaining the steps of this invention.

In the following detailed description, for the purposes of explanation and not limitation, representative embodiments disclosing specific details are set forth in order to provide a thorough understanding of an embodiment according to the present teachings. Descriptions of known systems, devices, materials, methods of operation and methods of manufacture may be omitted so as to avoid obscuring the description of the representative embodiments. Nonetheless, systems, devices, materials and methods that are within the purview of one of ordinary skill in the art are within the scope of the present teachings and may be used in accordance with the representative embodiments. It is to be understood that the terminology used herein is for purposes of describing particular embodiments only and is not intended to be limiting. The defined terms are in addition to the technical and scientific meanings of the defined terms as commonly understood and accepted in the technical field of the present teachings.

It will be understood that, although the terms first, second, third etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

The terminology used herein is for purposes of describing particular embodiments only and is not intended to be limiting. As used in the specification and appended claims, the singular forms of terms 'a', 'an' and 'the' are intended to include both singular and plural forms, unless the context clearly dictates otherwise. Additionally, the terms "comprises", and/or "comprising," and/or similar terms when used in this specification, specify the presence of stated features, elements, and/or components, but do not preclude the presence or addition of one or more other features, elements, components, and/or groups thereof. As used herein, the term "and/or" includes any and all combinations of one or more of the associated listed items.

Unless otherwise noted, when an element or component is said to be "connected to", "coupled to", or "adjacent to" another element or component, it will be understood that the element or component can be directly connected or coupled to the other element or component, or intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

The present disclosure, through one or more of its various aspects, embodiments and/or specific features or sub-components, is thus intended to bring out one or more of the advantages as specifically noted below. For purposes of explanation and not limitation, example embodiments disclosing specific details are set forth in order to provide a thorough understanding of an embodiment according to the present teachings. However, other embodiments consistent with the present disclosure that depart from specific details disclosed herein remain within the scope of the appended claims. Moreover, descriptions of well-known apparatuses and methods may be omitted so as to not obscure the description of the example embodiments. Such methods and apparatuses are within the scope of the present disclosure.

As described herein, data sets to be applied to a plurality of gene panels for genomic regions studied for inclusion in standardized clinical formats may be assessed using standardized quality control metrics. As a result, data sets to be applied to the plurality of gene panels may be filtered to sets of variants, and the sets of variants may be formatted in the standardized clinical formats. The standardization for the quality control metrics based on software may result in improved quality and consistency for sets of variants ultimately output to downstream applications, independent of the underlying formats for the data sets to be applied to the plurality of gene panels. The downstream applications may therefore be provided with standard workflows to bridge gaps between bioinformatics systems and standardized health records.

In more detail, as described herein, a rule engine microservice may link to files, such as .BED files and .VCF files, which contain genomic data sets, and return high-quality subsets of the data sets to be applied to the plurality of gene panels, based on common bioinformatics protocols and institution-specific thresholds. The teachings herein ensure traceability and storage of quality metadata together with high-quality variant results. Therefore, institution-specific quality control measures currently used to filter low-quality results may now be supplemented or replaced with the standard workflows described herein so as to enhance the quality and reliability of results of genetic sequencing in a way that allows for meeting increasing demands for analysis of variants detected in modern sequencing.

FIG. 1A illustrates a system 100A for assessing quality of genomic regions studied for inclusion in standardized clinical formats, in accordance with a representative embodiment.

The system 100A in FIG. 1A is a system for assessing quality of genomic regions studied for inclusion in standardized clinical formats and includes components that may be provided together or that may be distributed. The system 100A includes a database storage 115 and a server 140. The system 100A in FIG. 1A also includes the sequencing machines shown in FIG. 1A, including sequencing machine A 101, sequencing machine B 102, sequencing machine C 103, and additional sequencing machines up to and including sequencing machine 1109. The server 140 includes a controller 142. The number of sequencing machines which may provide sequencing data to a database storage 115 and/or server 140 is not limited to nine, and instead the system 100A may include more or less than nine sequencing machines.

The system 100A also includes a standard model 130. The standard model 130 may comprise data such as thresholds and instructions such as algorithms. The standard model 130 may be implemented by a memory that stores the standard model 130 and/or a processor that executes the instructions of the standard model 130.

The sequencing machines shown in FIG. 1A are used to sequence DNA. The sequencing machines output data sets to be applied to gene panels. A gene panel is a test that assesses one or more potential genetic causes of a suspected disorder(s), and is used, for example, to diagnose disorders with genetic and clinical heterogeneity. A gene panel is not limited to diagnostics, and instead can be used for identifying applicable therapies, clinical trials and more. Sequencing DNA using sequencing machines involves determining the order of the four chemical building blocks that make up a DNA molecule. The sequence of the four chemical building blocks corresponds to the type of genetic information carried in a particular gene. Sequence data may reflect genetic changes responsible for causing diseases. The human genome contains about 3 billion base pairs that spell out the instructions for making and maintaining a human being, though the sequencing machines in FIG. 1A may output data sets of less than 3 billion base pairs. For example, the sequencing machines shown in FIG. 1A are capable of sequencing individual genes, and outputting the DNA sequences as some or all of the data sets to the database storage 115. The sequencing machines may be provided in the same location (e.g., a facility) as the database storage 115, or may be distributed remove from each other and from the location of the database storage 115.

The server 140 is a computer for assessing quality of genomic regions studied for inclusion in standardized clinical formats. The server 140 is configured to retrieve the DNA sequences from the database storage 115. The server 140 may be connected to one or more communication networks via interfaces, and includes at least the controller 142 as shown. The controller 142 includes at least a memory 1422 and a processor 1421. The memory 1422 stores instructions and the processor 1421 executes the instructions. The server 140 may also access the standard model 130. The standard model 130 may be stored in a dedicated memory. Alternatively, in some embodiments, the server 140 may store the standard model 130 separately from the instructions stored in the memory 1422. Alternatively, in some embodiments, the database storage 115 may store the standard model 130 separately from metadata, region data and finding data described herein.

Figure 5:
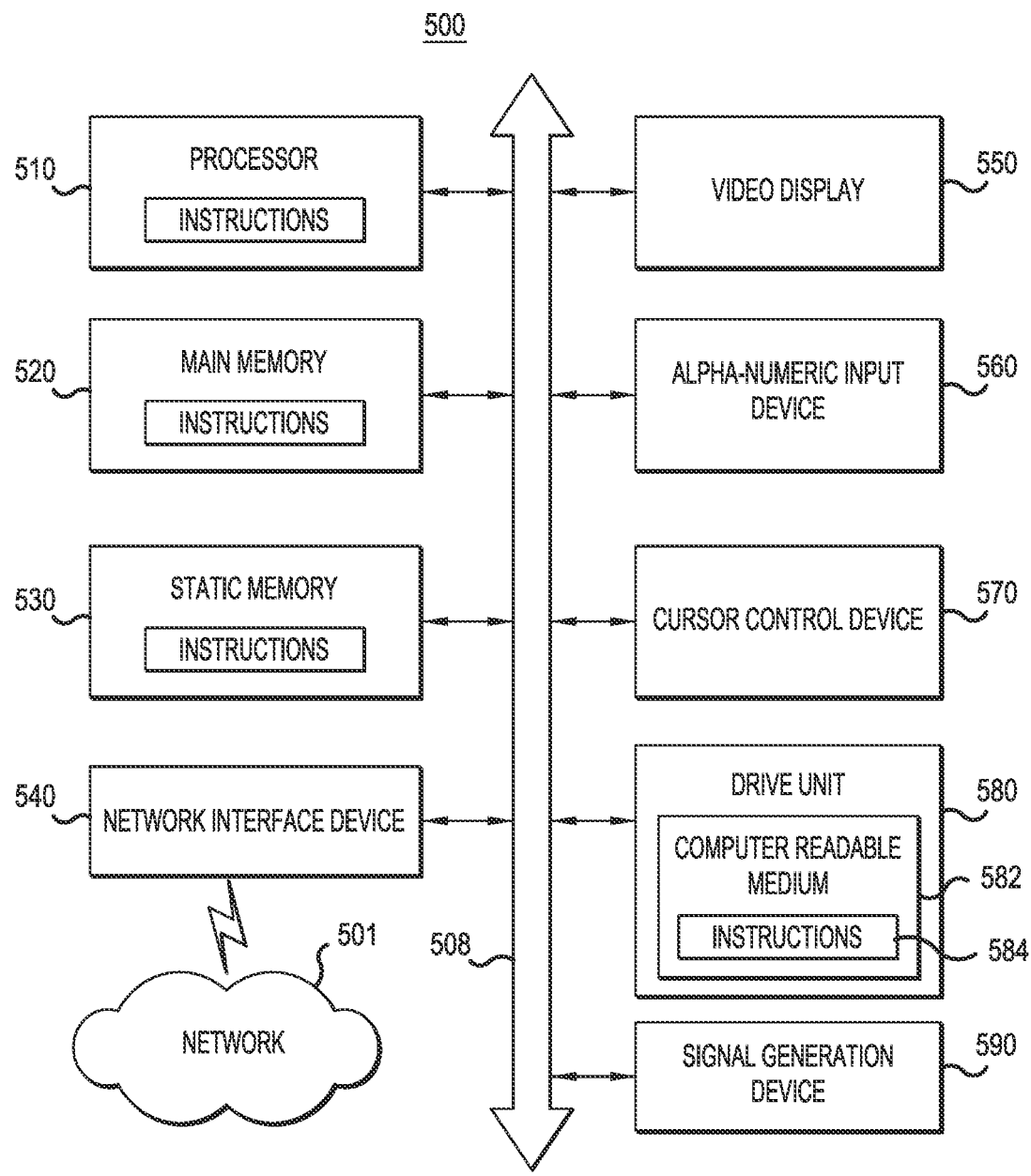
FIG. 5 illustrates a computer system, on which a method for assessing quality of genomic regions studied for inclusion in standardized clinical formats is implemented, in accordance with another representative embodiment.

The server 140 applies quality control measures to the data sets retrieved from the database storage 115. The quality control measures may result in or include filtering data of the data sets when the data does not meet metrics. The metrics may be absolute requirements required by a standard, or relative metrics set based on the type of data in the data set, based on the patient who sources the DNA sequenced by the sequencing machines, based on input from the institution that applies gene panels to the filtered data, or otherwise. It would be clear to the skilled person that variant filtering may be associated with both negative criteria, i.e. set of variants that do not meet the standardized quality control metrics, or with positive criteria, i.e. set of variants that meet the standardize quality control metrics. Hence, in some embodiments, the set of variants based on the quality control criteria can be used A computer that can be used to implement the controller 142 is depicted in FIG. 5, though such a computer may include more or fewer elements than depicted in FIG. 5. Whether implemented in a server 140 or not, the controller 142 includes the memory 1422 that stores instructions for implementing the quality control measures and the data sets output from the genomic sequencers as the data sets are being processed after retrieval from the database storage 115. The processor 1421 processes the instructions and applies the instructions to the data sets to implement the quality control measures. When executed by the processor 1421, the instructions cause the server 140 to execute a process that includes receiving data sets to be applied to the plurality of gene panels, and storing data sets to be applied to the plurality of gene panels in the memory 1422; applying standardized quality control metrics to the data sets to be applied to the plurality of gene panels; filtering, by the processor executing the instructions, each of the data sets to be applied to the plurality of gene panels to sets of variants and formatting the sets of variants in a clinical format, and outputting the sets of variants resulting from the filtering to a downstream application.

In FIG. 1A, the sequencing machines may provide the data sets to be applied to the plurality of gene panels to the database storage 115 at different times and from different locations, such that the server 140 is processing the data sets on-demand and not necessarily in real time. For example, the server 140 may retrieve data sets to be applied to the plurality of gene panels from the database storage 115 when they are provided by a facility such as a hospital or office. The data sets to be applied to the plurality of gene panels may be subject to processing by the server 140 in order to standardize the quality control processing for the genomic regions studied for inclusion in standardized clinical formats used by the facility, even if the data sets to be applied to the plurality of gene panels are not necessarily provided in real time.

Figure 1B:
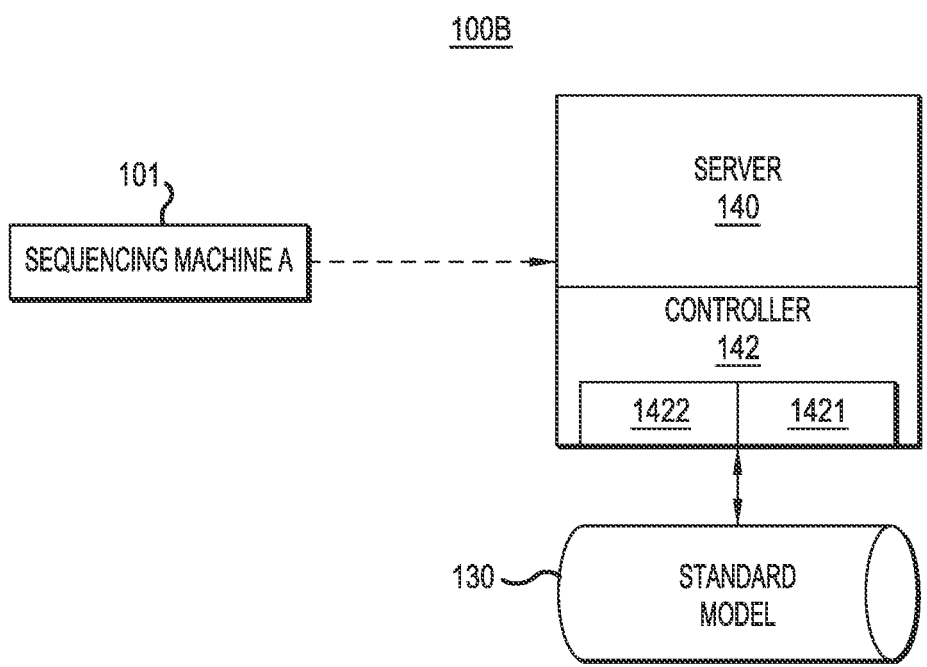
FIG. 1B illustrates another system for assessing quality of genomic regions studied for inclusion in standardized clinical formats, in accordance with a representative embodiment.

FIG. 1B illustrates a system 100B with a sequencing machine A 101, the server 140 and the standard model 130, but not the database storage 115 and the additional sequencing machines of FIG. 1A. In FIG. 1B, a sequencing machine A 101 may directly output data sets to be applied to the plurality of gene panels to the server 140, such as dynamically and in real-time as the data sets are produced by the sequencing machine A 101.

In either of FIG. 1A or FIG. 1B, the controller 142 may also include interfaces to other components and devices. The server 140 in either of FIG. 1A or FIG. 1B may be connected to additional devices such as a display, user input devices such as a keyboard, and may include interfaces to the additional devices. Interfaces between devices and components described herein may include ports, disk drives, wireless antennas, or other types of receiver circuitry, as well as user interfaces such as a mouse, a keyboard, a microphone, a video camera, a touchscreen display, or other forms of interactive user interfaces.

Although the controller 142 is shown as an element of the server 140, the controller 142 may be provided separate from the server 140, such as by a stand-alone controller or as a component of a device such as a workstation which also includes a display. The controller 142 may perform some of the operations described herein directly and may implement other operations described herein indirectly. That is, processes implemented by the controller 142 when the processor 1421 executes instructions from the memory 1422 may include steps not directly performed by the controller 142.

Figure 2:
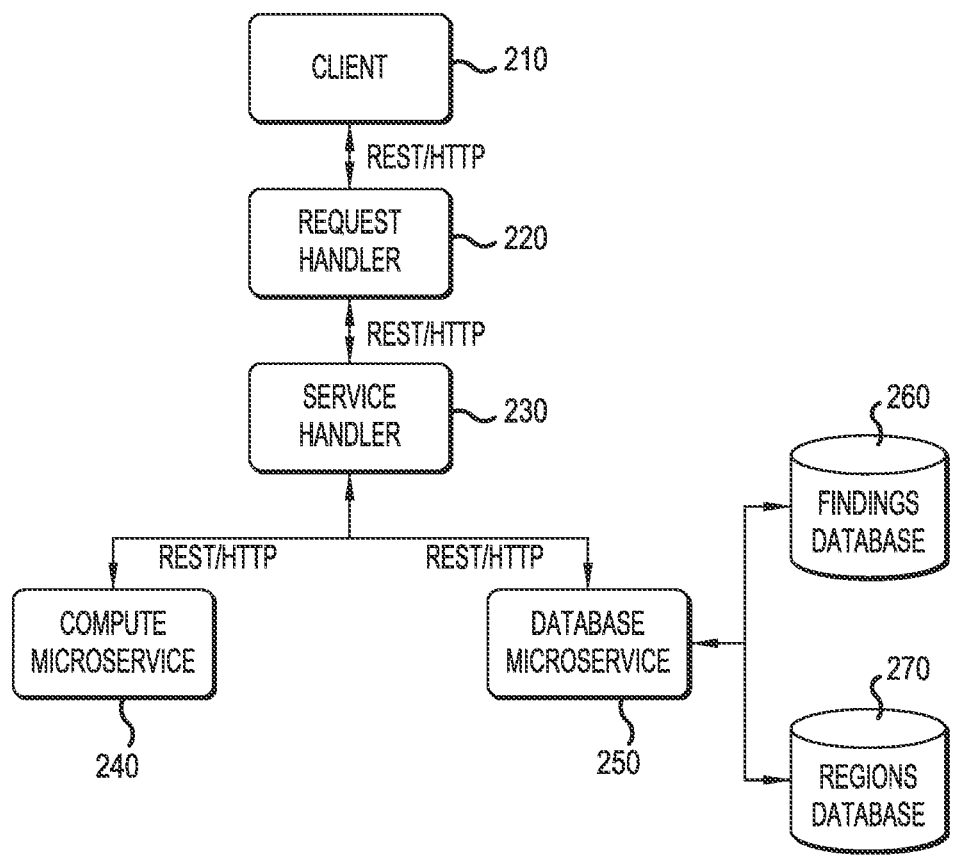
FIG. 2 illustrates a processing system for assessing quality of genomic regions studied for inclusion in standardized clinical formats, in accordance with a representative embodiment.

FIG. 2 illustrates a processing system for assessing quality of genomic regions studied for inclusion in standardized clinical formats, in accordance with a representative embodiment.

In FIG. 2, the processing system 200 includes a client 210, a request handler 220, a service handler 230, a compute service 240, a database service 250, a findings database 260 and a regions database 270.

The client 210 may be used by a user to read data such as the data sets provided from the database storage 115 or directly from the sequencing machines. The client 210 may also receive data from other sources, such as specific settings required for external applications implemented by institutions that will receive the filter data which has been subjected to the quality control measures described herein. For example, the client 210 may obtain variants, quality control metrics, and a pipeline identification from the data sets. The client 210 may also request coverage metrics. The client 210 may also be used to provide a response with full or partial quality control metadata and a job identification. A pipeline identification is an identifier that refers to a specific gene panel bioinformatics pipeline. Each pipeline has its own accompanying set of quality control thresholds and regions. Coverage metrics are metrics specific to a patient genomic sample and genomic regions that have been inspected. One example metric is average coverage across all regions for a sample, which represents the average number of reads at each region, and imparts confidence in the variants identified in those regions. Coverage metrics for a sample may be compared to thresholds set for the corresponding pipeline identification. If the coverage metrics do not meet the thresholds set for a particular region, the variants detected in that region may be filtered from the result. Coverage metrics can be computed from BAM/SAM files.

Examples of quality control metrics that may be used in the processing system 200 include variant-level metrics, including:
  minor allele frequency (MAF) must be at or above a minimum threshold
  number of reads supporting evidence of the variant (depth)
  percentage of supporting reads on forward and reverse strands (strand bias).
  functional impact: tools can be used to predict whether a variant would functionally alter the resulting protein; the variants with no functional impact are less likely to be clinically useful. These variants may be represented as scores in a VCF which may be incorporated as another threshold metric.

Examples of quality control metrics that may be used in the processing system 200 also include genomic-region-level variants, including:
  average depth (coverage per base)
  minimum depth at a given position in a region
  minimum depth of the region
  minimum percentage of variants read in a region finding the variant
  minimum average read depth of the region The client 210 may also be used by an administrator. For example, the client 210 may be used to create, delete or read a region table. Regions represent the gene panels to be employed by a clinical laboratory in day-to-day operations, and the region table may be stored as a table containing at least chromosome, start position, and end position for each gene, exon, transcript or other coordinate-based range. The client 210 may be used to request a .BED file or formatted text file or table identification. The client 210 may be used to provide a response with the table identification if successful, or an error notification if unsuccessful. The client 210 may also be used to provide a response with a success/fail indicator, or a table if successful or an error notification if unsuccessful.

For administrator functions, the client 210 may also be used to delete or read a findings table. Findings represent the variant and wildtype (WT) findings contained in a .VCF file or another database for each sample. The findings table may be stored as a table containing at least chromosome, start position, end position, reference nucleotide, and alternate nucleotide. For example, the client 210 may request a table identification. The client 210 may receive a response such as a success/fail indicator, or a table if successful or an error notification if unsuccessful.

Also for administrator functions, the client 210 may be used to create, delete or read quality control metadata for a region table. For example, the client 210 may request formatted JSON data and/or a table identification. JSON data is data formatted in the JavaScript Object Notation (JSON) format. The client 210 may receive a response with the table identification if successful or an error notification if unsuccessful, or a table if successful or an error notification if unsuccessful.

For additional administrator functions, the client 210 may be used to create or delete or read quality control metadata for a findings table. For example, the client 210 may be used to request formatted JSON data, and/or a table identification. The client 210 may receive a response with the table identification if successful or an error notification if unsuccessful, or a success/fail indicator, or a table if successful or an error notification if unsuccessful.

The request handler 220 may receive requests from the client 210. The request handler 220 may verify that a requesting user or administrator has permissions required for the request, such as through a separate authentication service, and otherwise deny a request. The request handler 220 may deliver requests to the service handler 230 and receive responses from the service handler 230. The request handler 220 also delivers responses to the client 210.

The service handler 230 receives requests from the request handler 220. The service handler 230 may execute requested functions on other elements of the processing system 200 including the database and compute services. The service handler 230 may create, delete or retrieve content in a database. The service handler 230 may create a new quality control test, using content retrieved from a database. The service handler 230 may retrieve quality control test results, such as by creating and/or storing new content in a database. The service handler 230 may also deliver results to the request handler 220.

The compute service 240 may compute quality control measures by applying algorithms to filter the data sets given certain inputs from the service handler 230. For example, the inputs from the service handler 230 may include a region table, region quality control thresholds and a BAM file. The inputs from the service handler may also or alternatively include a region table, region quality control thresholds and coverage metrics. The compute service 240 may use the inputs to compute coverage metrics and a pass/fail indicator. In another example, the inputs from the service handler 230 may include a findings table and quality control thresholds for findings in the findings table. The compute service 240 may compute variant metrics and a pass/fail indicator. As yet another example, the inputs from the service handler 230 may include coverage metrics and variant metrics. The compute service 240 may compute a total quality control report.

The compute service 240 may overlay coverage metrics with the region table to determine metrics in the ranges of the coverage metrics as well as overall metrics at the genome level. The metrics may then be compared to thresholds to determine a pass/fail indicator indicating whether the metrics meet the thresholds. In another example, individual variant metrics may be overlayed with findings thresholds to determine a pass/fail indicator.

The compute service 240 may be a rule engine microservice. As a rule engine microservice, the compute service 240 may be responsible for accepting configuration of the user for any type of quality control metric. The metrics, at the variant level, may include minor allele frequency (MAF), number of reads supporting evidence of the variant (depth), the ratio of supporting reads on the forward and reverse strands (strand bias), and others. The metrics, at the at the genomic region level, may include average depth (the coverage per base), the minimum depth at a given position in a region, and others as well. As a rule engine microservice, the compute service 240 may also accept configuration for set thresholds from users. As an example, a configuration for a threshold set from a user may include a requirement that the average coverage per base must be greater than or equal to 500×. The compute service 240 may operate as all or part of an application programming interface (API), and can be updated to include new quality control metrics, calculations, and thresholds. The application programming interface may accept application programming interface calls from external applications, such as downstream applications used for clinical purposes. The application programming interface may be implemented to enable retrieval of quality control metadata in a standardized format, and may be configured to interface with external application such as information technology (IT) systems in hospitals.

The compute service 240 may apply a standard model of quality control metrics to data sets to be applied to the plurality of gene panels, whether from the database storage 115 or directly from the sequencing machines in FIG. 1A and FIG. 1B. While allowing for user designation of thresholds and particular quality control metrics, the standard model may ensure that uniform minimum quality control standards are applied by the compute service 240, or at least made available to users of the compute service 240.

The database service 250 may create and read the database(s). The database(s) in FIG. 2 include the region table(s), the region table quality control threshold data template(s), finding table(s), finding table quality control results data template(s) and alignments. The region table(s) include contents of a .BED file describing genomic regions. The region table quality control threshold data template(s) include pass/fail thresholds for each quality control metric. Examples of quality control metrics include total average read depth, and average read depth at each region. The finding table(s) may include variant call results, including the finding and accompanying quality information. The finding table(s) may also include pass/fail indicators for each variant call result based on finding-specific quality control. The findings table quality control results data template(s) may include pass/fail thresholds for each quality control attribute. Quality control attributes include minor allele frequency, depth, strand bias and so on. The alignment(s) may include a BAM file to compute region quality control thresholds when they are not provided by the client 210.

A database system may include all three of the database service 250, the findings database 260 and the regions database 270. Several key components of the database system are regions, findings, and quality control metadata. The regions represent the series of gene panels a clinical laboratory may employ in day-to-day operations stored as a table containing at least chromosome, start position, and end position for each gene, exon, transcript, or other coordinate-based range. There may be any number of region tables for a particular laboratory or organization. Findings represent the variant and WT (wildtype) findings contained in the .VCF file or other database for each sample and are stored as a table containing at least chromosome, start position, end position, reference nucleotide, and alternate nucleotide. The number of findings is highly variable depending on the sample, extent of the study (which can range between a handful to thousands of genes), and quality control thresholds governed by the microservice. The microservice facilitates interactions between .VCF and .BED files and the database system. Regions and findings are only stored if they are cleared by the microservice, having passed the quality control steps described above. The database microservice may implement quality control metadata using the two tables representing the quality control metadata for regions and findings. The types of quality control metadata include the metrics described herein.

Figure 3:
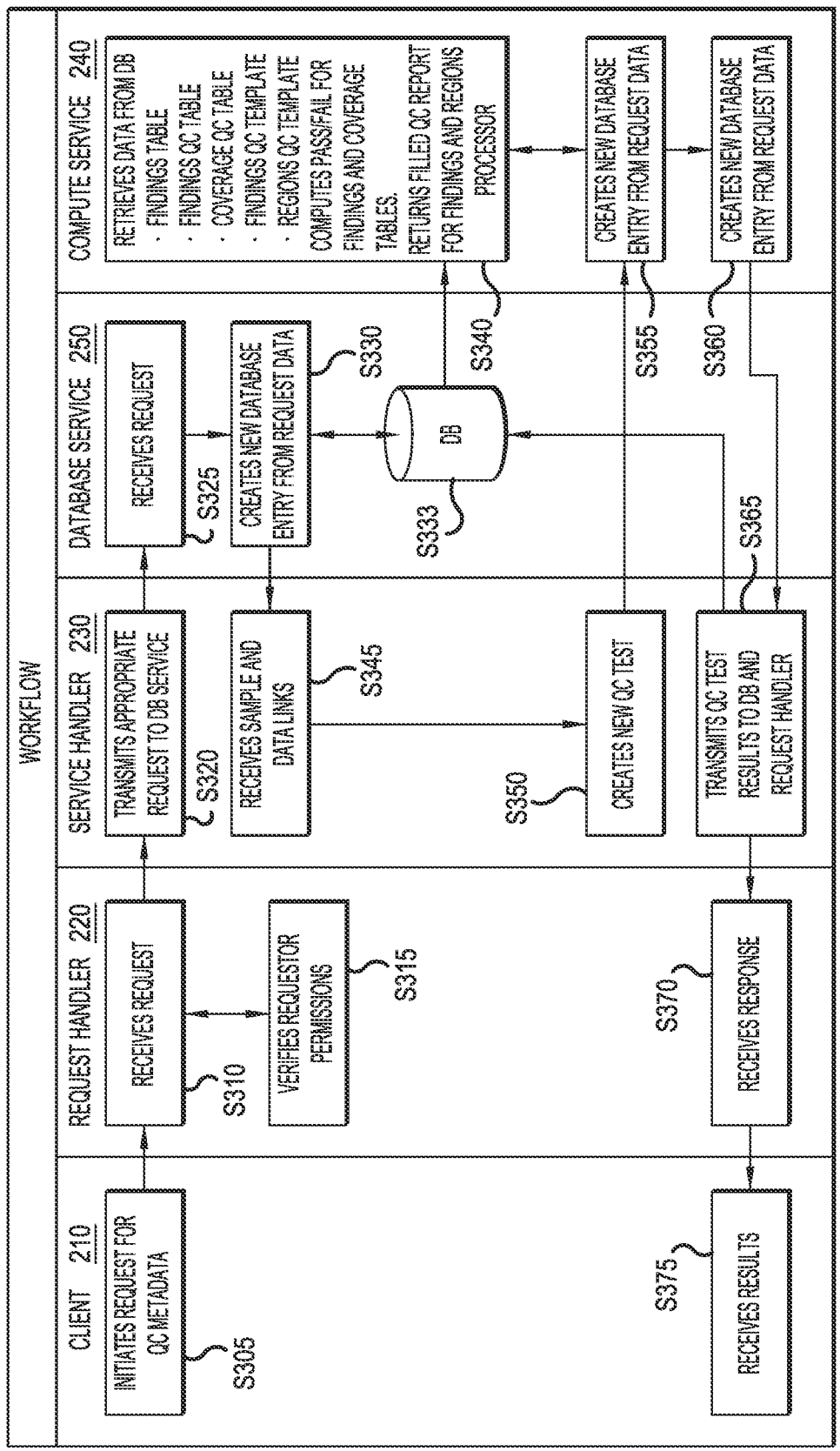
FIG. 3 illustrates a processing flow for assessing quality of genomic regions studied for inclusion in standardized clinical formats using the processing system of FIG. 2, in accordance with a representative embodiment.

FIG. 3 illustrates a processing flow for assessing quality of genomic regions studied for inclusion in standardized clinical formats using the processing system of FIG. 2, in accordance with a representative embodiment.

In FIG. 3, the client 210 initiates a request for quality control (QC) metadata at S305. The request for quality control metadata is sent from the client 210 to the request handler 220.

At S310, the request handler 220 receives the request from the client 210. At S315, the request handler verifies that the requesting user or administrator has the appropriate permissions to make the request and receive an answer. Accordingly, the request at S305 may include information identifying the requestor, or a type of the requestor such as a title, or another form of identifying information that either specifically or generically identifies the requestor. The request handler 220 transmits the request to the service handler 230 after verifying the requestor permissions at S315.

At S320, the service handler 230 receives the request from the request handler 220 and transmits an appropriate request to a database service (DB service).

At S325, the database service receives the request from the service handler 230.

At S330, the database service 250 creates a new database entry from the data corresponding to the request received at S325. The new database entry is entered to the database (DB) at S333.

At S340, the compute service 240 retrieves data from the database. The data retrieved from the database may include data sets from genomic sequencers along with metadata and settings corresponding to the data sets. The database in FIG. 3 may be a database system including the database service 250, the findings database 260 and the regions database 270 in FIG. 2. The data retrieved from the database in FIG. 3 may also include a findings table, a findings quality control table, a coverage quality control table, a findings quality control template, and a regions quality control template. The compute service 240 computes a pass/fail determination for the findings and coverage tables, and returns a filled quality control report for a findings and regions processor.

At S345, the service handler 230 receives sample and data links from the database service 250.

At S350, the service handler 230 creates a new quality control test. At S355, the service handler 230 provides the new quality control test to the compute service 240.

At S355, the compute service processes quality control test instructions based on the new quality control test. The processing at S355 may be performed based on the data retrieved by the compute service 240 from the database service 250 at S340. The quality control test instructions instruct the compute service to perform processing which may include applying one or more quality control tests to one or more data set(s) from one or more genomic sequencers as described herein.

At S360, the compute service 240 delivers the quality control test results to the service handler 230.

At S365, the service handler 230 transmits the quality control test results to the database and to the request handler 220.

At S370, the request handler 220 receives the response from the service handler 230.

At S375, the client 210 receives the results from the request handler 220. The results from the request handler 220 may include one or more data set(s) to which a standard model of quality control metrics is applied to result in a filtered data set that meets the quality control standards imposed by the standard model. An application programming interface may be used for the compute service 240 to apply the standard model and impose the quality control metrics of the standard model.

FIG. 4A illustrates a method for assessing quality of genomic regions studied for inclusion in standardized clinical formats, in accordance with a representative embodiment.

In FIG. 4A, the method starts at S410 with creating a standard data model representative of quality control metrics. The standard data model may be used as a standard so that quality control metrics are uniformly applied to genomic regions and can be used to output results in a standardized clinical format. The standard data model may be created in a JSON format or an extensible markup language (XML) format with value pairs. For example, the standard data model may include all quality control metrics for a quality control standard, even if one or more such quality control metrics are elective or adjustable. The standard data model may provide mechanisms for computing the quality control metrics from raw data, such as via equations.

At S420, the method of FIG. 4A includes creating descriptions for how each quality metric is calculated. The descriptions may be created in python script. The descriptions may include supported features and metrics.

At S430, the method of FIG. 4A includes describing features and metrics which are supported by the API which will be used to implement the assessments described herein. The features and metrics may be all possible or known features and metrics, or a subset of all features and metrics such as a subset confirmed via a standardization committee. For example, an API may support 15 metrics, or may support 100 or more metrics. The API may provide functionality described herein to numerous different downstream applications and facilities/institutions. For example, since the quality control metrics described herein may be standardized, the API may be used to ensure that data sets from genomic sequencers comply to standardized quality control metrics before they are provided for testing to gene panels.

At S440, sequencing is performed on genetic regions of a genetic sample, and the sequencing results are output.

At S450, the sequencing results are applied to the application programming interface (API) described herein. The API applies quality control metrics to the sequencing results. The data sets of the sequencing results are subjected to standardized quality control measures so that filtered results are standardized before being provided to institutions for use by/for/in external applications.

At S470, standardized quality control metrics are applied from the API. For example, at S470, the method may include mapping a standardized model to each data set for each region. The standardized model may include the standardized quality control metrics applied from the API, even if and when a user is allowed to configure individual quality control metrics in the standardized model. The sets of variants resulting from filtering may be output to one or more downstream applications, such that the sets of variants are made accessible to external applications.

FIG. 4B illustrates a processing method for assessing quality of genomic regions studied for inclusion in standardized clinical formats, in accordance with a representative embodiment. In FIG. 4B, a first metric is applied at S451, and then an algorithm applied via the API increments at S452. At S457, the algorithms determine whether the API is done. The API may be done when all quality control metrics have been applied, or when a genomic region has failed a quality control metric such that the genomic region need not be subject to additional quality control metrics. If the processing of the genomic region(s) is done (S457=Yes), the process finishes at S458. If the processing of the genomic region(s) is not done (S457=No), the next metric is applied via the API at S459 and the process returns to S452 to increment.

The process of FIG. 4B is representative of quality control measures applied by a single thread of instructions. For example, quality control metrics may be applied to genomic regions sequentially until all quality control metrics are applied or until a genomic region does not satisfy the quality control metric.

FIG. 4C illustrates another processing method for assessing quality of genomic regions studied for inclusion in standardized clinical formats, in accordance with a representative embodiment.

At S461, a first metric is applied. A status of the quality control process is updated at S462, such as by updating a register value or by updating a counter at a dedicated portion of a memory used to track statuses of quality control processes.

At S463, a next thread and/or core of a multi-core processor checks the status. At S467, the algorithms determine whether the API is done. The API may be done when all quality control metrics have been applied, or when a genomic region has failed a quality control metric such that the genomic region need not be subject to additional quality control metrics. If the processing of the genomic region(s) is done (S467=Yes), the process finishes at S468. If the processing of the genomic region(s) is not done (S467=No), the next metric is applied via the API at S469 and the process returns to S462 to update status.

Using different cores of a multi-core processor, each of a plurality of cores may apply a different standardized quality control metric to data sets to be applied to a plurality of gene panels. Algorithms may be synchronized to process large volumes of DNA data by systematically applying quality control metrics and marking completion of each quality control metric for a gene once the quality control metric has been applied.

The process of FIG. 4C is representative of quality control measures applied by multiple threads of instructions running simultaneously on different genomic regions, such as when a multi-core processor is programmed to apply the quality control measures on large volumes of genomic regions. Each genomic region or each set of genomic regions may be subjected to quality control processing by a single thread for a single quality control metric, and then the status is updated to let the next thread know that the next quality control processing may be applied. In this way, a multi-core processor may apply multiple quality control tests to volumes of genomic regions efficiently. Each thread may mark that a quality control metric is not met using the status fields, such as by marking a status to complete or to fail such that the sequencing results are not included in the standardized clinical format which results from the quality control measures described herein.

As an example of how the methods and systems herein can be used, a clinical laboratory may use a next generation healthcare standard framework for storage of clinical-grade genomics results for the clinical laboratory's use in downstream applications and interoperability with third party systems. The clinical laboratory may move both prospective and retrospective data to the new framework, so that previous datasets may be integrated with the new model. The collection of gene panels offered by the clinical laboratory, in the form of .BED files, may be incorporated into the database system via the rule engine microservice API. Then, the quality control configurations and thresholds may be imported for regions and findings. The clinical laboratory may require reporting of the following for regions: average depth for each region (>=500 reads/nucleotide) and the overall (average of region averages) depth (>=500 reads/ nucleotide). The following may also be reported for findings: MAF (>=0.05), depth (>=500 reads), and strand odds ratio (<=4 SOR for SNPs and <=10 SOR for insertions and deletions). The .VCF files for retrospective tests may bee sent to the rule engine microservice, where only the findings (variants and wildtype) satisfying the thresholds are approved for importing into the database system. The next generation healthcare standard framework is thus enabled to interact with the rule engine microservice and underlying database system to interoperate with other applications.

FIG. 5 illustrates a computer system, on which a method for assessing quality of genomic regions studied for inclusion in standardized clinical formats is implemented, in accordance with another representative embodiment.

Referring to FIG. 5, the computer system 500 includes a set of software instructions that can be executed to cause the computer system 500 to perform any of the methods or computer-based functions disclosed herein. The computer system 500 may operate as a standalone device or may be connected, for example, using a network 501, to other computer systems or peripheral devices. In embodiments, a computer system 500 performs logical processing based on digital signals received via an analog-to-digital converter.

In a networked deployment, the computer system 500 operates in the capacity of a server or as a client user computer in a server-client user network environment, or as a peer computer system in a peer-to-peer (or distributed) network environment. The computer system 500 can also be implemented as or incorporated into various devices, such as a server or another type of computer such as a workstation that includes the controller 142 in FIG. 1A or FIG. 1B, a stationary computer, a mobile computer, a personal computer (PC), a laptop computer, a tablet computer, or any other machine capable of executing a set of software instructions (sequential or otherwise) that specify actions to be taken by that machine. The computer system 500 can be incorporated as or in a device that in turn is in an integrated system that includes additional devices. In an embodiment, the computer system 500 can be implemented using electronic devices that provide voice, video or data communication. Further, while the computer system 500 is illustrated in the singular, the term "system" shall also be taken to include any collection of systems or sub-systems that individually or jointly execute a set, or multiple sets, of software instructions to perform one or more computer functions.

As illustrated in FIG. 5, the computer system 500 includes a processor 510. The processor 510 may be considered a representative example of the processor 1421 of the controller 142 in FIG. 1A and FIG. 1B and executes instructions to implement some or all aspects of methods and processes described herein. The processor 510 is tangible and non-transitory. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. The processor 510 is an article of manufacture and/or a machine component. The processor 510 is configured to execute software instructions to perform functions as described in the various embodiments herein. The processor 510 may be a general-purpose processor or may be part of an application specific integrated circuit (ASIC). The processor 510 may also be a microprocessor, a microcomputer, a processor chip, a controller, a microcontroller, a digital signal processor (DSP), a state machine, or a programmable logic device. The processor 510 may also be a logical circuit, including a programmable gate array (PGA), such as a field programmable gate array (FPGA), or another type of circuit that includes discrete gate and/or transistor logic. The processor 510 may be a central processing unit (CPU), a graphics processing unit (GPU), or both. Additionally, any processor described herein may include multiple processors, parallel processors, or both. Multiple processors may be included in, or coupled to, a single device or multiple devices.

The term "processor" as used herein encompasses an electronic component able to execute a program or machine executable instruction. References to a computing device comprising "a processor" should be interpreted to include more than one processor or processing core, as in a multi-core processor. A processor may also refer to a collection of processors within a single computer system or distributed among multiple computer systems. The term computing device should also be interpreted to include a collection or network of computing devices each including a processor or processors. Programs have software instructions performed by one or multiple processors that may be within the same computing device or which may be distributed across multiple computing devices.

The computer system 500 further includes a main memory 520 and a static memory 530, where memories in the computer system 500 communicate with each other and the processor 510 via a bus 508. Either or both of the main memory 520 and the static memory 530 may be considered representative examples of the memory 1422 of the controller 142 in FIG. 1A and FIG. 1B, and store instructions used to implement some or all aspects of methods and processes described herein. Memories described herein are tangible storage mediums for storing data and executable software instructions and are non-transitory during the time software instructions are stored therein. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. The main memory 520 and the static memory 530 are articles of manufacture and/or machine components. The main memory 520 and the static memory 530 are computer-readable mediums from which data and executable software instructions can be read by a computer (e.g., the processor 510). Each of the main memory 520 and the static memory 530 may be implemented as one or more of random access memory (RAM), read only memory (ROM), flash memory, electrically programmable read only memory (EPROM), electrically erasable programmable read-only memory (EEPROM), registers, a hard disk, a removable disk, tape, compact disk read only memory (CD-ROM), digital versatile disk (DVD), floppy disk, blu-ray disk, or any other form of storage medium known in the art. The memories may be volatile or non-volatile, secure and/or encrypted, unsecure and/or unencrypted.

"Memory" is an example of a computer-readable storage medium. Computer memory is any memory which is directly accessible to a processor. Examples of computer memory include, but are not limited to RAM memory, registers, and register files. References to "computer memory" or "memory" should be interpreted as possibly being multiple memories. The memory may for instance be multiple memories within the same computer system. The memory may also be multiple memories distributed amongst multiple computer systems or computing devices.

As shown, the computer system 500 further includes a video display unit 550, such as a liquid crystal display (LCD), an organic light emitting diode (OLED), a flat panel display, a solid-state display, or a cathode ray tube (CRT), for example. Additionally, the computer system 500 includes an input device 560, such as a keyboard/virtual keyboard or touch-sensitive input screen or speech input with speech recognition, and a cursor control device 570, such as a mouse or touch-sensitive input screen or pad. The computer system 500 also optionally includes a disk drive unit 580, a signal generation device 590, such as a speaker or remote control, and/or a network interface device 540.

In an embodiment, as depicted in FIG. 5, the disk drive unit 580 includes a computer-readable medium 582 in which one or more sets of software instructions 584 (software) are embedded. The sets of software instructions 584 are read from the computer-readable medium 582 to be executed by the processor 510. Further, the software instructions 584, when executed by the processor 510, perform one or more steps of the methods and processes as described herein. In an embodiment, the software instructions 584 reside all or in part within the main memory 520, the static memory 530 and/or the processor 510 during execution by the computer system 500. Further, the computer-readable medium 582 may include software instructions 584 or receive and execute software instructions 584 responsive to a propagated signal, so that a device connected to a network 501 communicates voice, video or data over the network 501. The software instructions 584 may be transmitted or received over the network 501 via the network interface device 540.

In an embodiment, dedicated hardware implementations, such as application-specific integrated circuits (ASICs), field programmable gate arrays (FPGAs), programmable logic arrays and other hardware components, are constructed to implement one or more of the methods described herein. One or more embodiments described herein may implement functions using two or more specific interconnected hardware modules or devices with related control and data signals that can be communicated between and through the modules. Accordingly, the present disclosure encompasses software, firmware, and hardware implementations. Nothing in the present application should be interpreted as being implemented or implementable solely with software and not hardware such as a tangible non-transitory processor and/or memory.

In accordance with various embodiments of the present disclosure, the methods described herein may be implemented using a hardware computer system that executes software programs. Further, in an exemplary, non-limited embodiment, implementations can include distributed processing, component/object distributed processing, and parallel processing. Virtual computer system processing may implement one or more of the methods or functionalities as described herein, and a processor described herein may be used to support a virtual processing environment.

Accordingly, assessing quality of genomic regions studied for inclusion in standardized clinical formats provides a standard workflow to bridge the gap between bioinformatics systems and standardized health records. As described herein, a rule engine microservice may link to .BED and .VCF files and return a high-quality subset of the data in these files, based on common bioinformatics protocols and institution-specific thresholds, while still being amenable for incorporation into next generation standards frameworks for healthcare. The teachings herein ensure traceability and storage of quality metadata alongside high-quality variant results. Therefore, institution-specific quality control measures currently used to filter low-quality results may now be supplemented or replaced with a standard workflow so as to enhance reliability of results stored in medical systems in a way that allows for handling the number of variants detected in modern sequencing. The teachings here may be used in systems which provide services to unify .VCF, .BED, and quality metadata for interoperability with next generation healthcare systems such as HL7 FHIR.

Although assessing quality of genomic regions studied for inclusion in standardized clinical formats has been described with reference to several exemplary embodiments, it is understood that the words that have been used are words of description and illustration, rather than words of limitation. Changes may be made within the purview of the appended claims, as presently stated and as amended, without departing from the scope and spirit of assessing quality of genomic regions studied for inclusion in standardized clinical formats in its aspects. Although assessing quality of genomic regions studied for inclusion in standardized clinical formats has been described with reference to particular means, materials and embodiments, assessing quality of genomic regions studied for inclusion in standardized clinical formats is not intended to be limited to the particulars disclosed; rather assessing quality of genomic regions studied for inclusion in standardized clinical formats extends to all functionally equivalent structures, methods, and uses such as are within the scope of the appended claims.

The illustrations of the embodiments described herein are intended to provide a general understanding of the structure of the various embodiments. The illustrations are not intended to serve as a complete description of all of the elements and features of the disclosure described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The skilled person would understand that the terms described in the application may have a specific meaning within the context of this invention or the general meaning within the art. For instance, the term "standardized clinical formats" may mean to standardized reports within the field of medical documentation, such as the ones subject to FHIR HL7 standard. Other example may include the term "standardized quality control metrics" may mean quality control metrics applicable to a specific situation in hand. Considering that there are no standard quality control metrics accepted as a standard worldwide in the field of genomics, and it is a developing field, this is a generalization of the word "standard". The quality control metrics can include, but are not limited to, sample quality control, library quality control, sequencing quality control, sequence analysis metrics (yield, error rate, %>=Q30, Density (K/mm2), Cluster PF (%) and Phas/Prephas (%), etc.), sequencing reads and others. "Standardized model" within the context of the present invention may mean a model, which includes standardized features, such as standardized quality scores. The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The preceding description of the disclosed embodiments is provided to enable any person skilled in the art to practice the concepts described in the present disclosure. As such, the above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents and shall not be restricted or limited by the foregoing detailed description.

The invention claimed is:

1. A method for assessing quality of genomic regions studied for inclusion in standardized clinical formats, the method comprising:
   receiving data sets for a plurality of gene panels;
   applying, by a processor executing instructions, standardized quality control metrics to the data sets for the plurality of gene panels;
   filtering, by the processor executing the instructions, each of the data sets for the plurality of gene panels to sets of variants that do not meet the standardized quality control metrics, and formatting the sets of variants in a clinical format, and
   outputting the sets of variants resulting from the filtering to a downstream application.

2. The method of claim 1, wherein formats for the data sets subject to the standardized quality control metrics comprise .VCF and .BED file extensions.

3. The method of claim 1, wherein the data sets are received from a sequencing machine.

4. The method of claim 1, wherein the standardized quality control metrics include a metric for a depth of sequencing for a region.

5. The method of claim 1, wherein the standardized quality control metrics include a metric for a percentage of variants in a region.

6. The method of claim 1, wherein the standardized quality control metrics are applied by a microservice which retrieves studied regions and applies the standardized quality control metrics to the studied regions.

7. The method of claim 1, wherein the processor executes the instructions to implement a rule engine microservice that outputs a subset of each data set of a gene panel, formatted in the clinical format.

8. The method of claim 1, wherein the standardized quality control metrics applied by the processor are customizable.

9. The method of claim 1, further comprising mapping a standardized model to each data set for each region.

10. A server for assessing quality of genomic regions studied for inclusion in standardized clinical formats, comprising:
a memory that stores instructions and data sets for a plurality of gene panels; and
a processor that processes the instructions, wherein, when executed by the processor, the instructions cause the server to execute a process comprising:
receiving data sets for the plurality of gene panels, and storing the data sets for the plurality of gene panels in the memory;
applying standardized quality control metrics to the data sets for the plurality of gene panels;
filtering, by the processor executing the instructions, each of the data sets for the plurality of gene panels to sets of variants that do not meet the standardized quality control metrics, and formatting the sets of variants in a clinical format, and
outputting the sets of variants resulting from the filtering to a downstream application.

11. The server of claim 10, wherein the instructions further cause the server to:
output the sets of variants resulting from the filtering to a database system that stores the sets of variants, and makes the sets of variants accessible to external applications.

12. The server of claim 11, wherein instructions comprise an application programming interface which accepts application programming interface calls from the external applications.

13. The server of claim 10,
wherein the processor comprises a multi-core processor, and
wherein each of a plurality of cores of the multi-core processor apply a different standardized quality control metric to the data sets for the plurality of gene panels.

14. The server of claim 10, wherein the standardized quality control metrics are configurable by a user.

15. The server of claim 10, wherein the standardized quality control metrics include variant-level metrics and region-level metrics.

16. A computer program for assessing quality of genomic regions studied for inclusion in standardized clinical formats,
wherein, when executed by a processor, the instructions cause a computer to:
receive data sets for a plurality of gene panels, and store the data sets to for the plurality of gene panels in a memory;
apply standardized quality control metrics to the data sets for the plurality of gene panels;
filter each of the data sets for the plurality of gene panels to sets of variants that do not meet the standardized quality control metrics, and format the sets of variants in a clinical format, and
output the sets of variants resulting from the filtering to a downstream application.

* * * * *